United States Patent [19]

Schoenberg

[11] Patent Number: 5,037,843

[45] Date of Patent: Aug. 6, 1991

[54] ANTIMICROBIAL PRESERVATIVE SYSTEM AND METHOD COMPRISING A FORMALDEHYDE SUBSTITUTED HYDANTOIN

[75] Inventor: Thomas G. Schoenberg, Brookfield, Ill.

[73] Assignee: The McIntyre Group, Ltd., University Park, Ill.

[21] Appl. No.: 488,654

[22] Filed: Mar. 5, 1990

[51] Int. Cl.$^5$ ............... A61K 31/415; A61K 31/265; A61K 31/235; A61K 31/115

[52] U.S. Cl. ................................ 514/389; 514/392; 514/512; 514/544; 514/693; 514/696; 514/738

[58] Field of Search ............... 514/392, 389, 738, 544, 514/696, 693, 512; 548/308, 312

[56] References Cited

U.S. PATENT DOCUMENTS

| | | | |
|---|---|---|---|
| 2,155,863 | 4/1939 | Jacobson | 260/69 |
| 2,532,278 | 12/1950 | Chadwick | 260/67.5 |
| 2,955,057 | 10/1960 | Gagliardi et al. | 117/139.4 |
| 3,987,184 | 10/1976 | Foelsch | 424/273 |
| 4,172,140 | 10/1979 | Shull et al. | 424/273 |
| 4,345,936 | 8/1982 | Thibault et al. | 71/92 |
| 4,454,133 | 6/1984 | Berke et al. | 514/388 |
| 4,581,351 | 4/1986 | Berke et al. | 514/188 |

FOREIGN PATENT DOCUMENTS 0327220 9/1989 European Pat. Off.

OTHER PUBLICATIONS

Chem. Abstracts, 65:723b (1966).
Glydant Product Bulletin, Glyco Chemicals, Inc. (9/78).
Glyco Product Bulletin, G-41, Glyco Chemicals, Inc. (1/74).
Product Guide, McIntyre Group Ltd., p. 16 (2/89).
Germaben II Product Bulletin, Sutton Laboratories, Inc. (undated).
Parabens Product Bulletin, Napp Chemicals (undated).
Markland, W. R., "Paraben Combinations with Other Preservatives", Norda Briefs, No. 485, Norda Inc. (1978).
Parker, Malcolm S., "Preservatives in Combination", Soap, Perf., Cosmet., 223-224 (Apr., 1973).
Schanno et al., "Evaluation of 1,3-dimethylol-5,-5-dimethyl Hydantoin as a Cosmetic Preservative", J. Soc. Cosmet. Chem., 31, 85-96 (1980).
Jacobs et al., "The Influence of pH, Emulsifier, and Accelerated Ageing upon Preservative Requirements of O/W Emulsions", J. Soc. Cosmet. Chem., 26, 105-117 (1975).
CTFA Cosmetic Ingredient Dictionary, Third Edition, Supplement p. 22, The Cosmetic, Toiletry and Fragrance Assocation, Inc. (1985).

Primary Examiner—Glennon H. Hollrah
Assistant Examiner—Gary Hollinden
Attorney, Agent, or Firm—Olson & Hierl

[57] ABSTRACT

A method of preparing an antimicrobial preservative system in a substantially anhydrous liquid form is disclosed. The antimicrobial preservative system inhibits or retards microbial growth when an effective antimicrobial amount is subsequently added to a medium capable of supporting undesirable microbial growth. More particularly, the preservative system comprises a condensation product of a 5,5-disubstituted hydantoin and formaldehyde prepared in the presence of a substantially anhydrous, water-miscible, solvent and an alkalizing agent. Also disclosed is a cold-stable, substantially anhydrous liquid preservative system comprising 1,3-dimethylol-5,5-dimethylhydantoin alone or in combination with an effective antimicrobial amount of at least one paraben preservative prepared by an embodiment of the disclosed method.

33 Claims, No Drawings

ANTIMICROBIAL PRESERVATIVE SYSTEM AND METHOD COMPRISING A FORMALDEHYDE SUBSTITUTED HYDANTOIN

TECHNICAL FIELD

This invention relates to preservative systems useful in the production of various consumer products, such as personal care products and industrial products. In particular, the invention relates to an antimicrobial preservative system to prevent or retard microbial growth when it is included in an aqueous medium containing sufficient water to support the growth of microorganisms. More particularly, this invention relates to a method of preparing a liquid antimicrobial preservative system comprising a condensation product of a 5,5-disubstituted hydantoin and formaldehyde in substantially anhydrous form.

BACKGROUND ART

Antimicrobial preservatives are commonly included in aqueous consumer products and industrial products to prolong the useful life of the product during storage and usage. Such consumer products include personal care products, household products, pet-grooming products and like products which are handled by or come in contact with the skin of the user. Industrial products made up as aqueous media can also come in contact with the skin of the user. The presence of water in such aqueous media can support the growth of microorganisms. While some microorganisms can be innocuous, others can be pathogenic to humans.

Microbial growth or contamination also can and frequently does cause deterioration of the product while the is in the trade channels and in the hands of a consumer. This deterioration can undesirably alter a product's attributes rendering it physically or chemically unaesthetic, or shorten the product's useful life making it unmarketable and, in some instances, even be injurious to humans. Thus antimicrobial preservatives are desirable and necessary for inclusion in aqueous consumer products, and cosmetics in particular.

The term "antimicrobial preservative" as used herein refers to a compound or substance that kills microorganisms or prevents, inhibits or retards their growth and reproduction and is included in a product only at a concentration sufficient to prevent spoilage or prevent the growth of inadvertently added microorganisms. Such an antimicrobial preservative extends the useful life of a product but does not contribute to the claimed effects of the product.

The term "personal care products" as used herein refers to health and cosmetic beauty aid products generally recognized as being formulated for beautifying and grooming the skin and hair. For example, personal care products include cosmetics, toiletries, and over-the-counter pharmaceutical products intended for topical usage.

The term "household products" as used herein refers to products specially formulated for cleaning or caring for hard surfaces, clothing and the like for use in homes or institutions. For example, household products include detergents, cleansers, fabric softeners, room deodorizers, soaps and the like.

The term "industrial products" as used herein refers to products made up in aqueous medium for use in the industrial workplace or for maintaining hard surfaces and which may come in contact with the worker's hands or skin. For example, industrial products can include water-based paints, cutting oils, latex solutions and the like in which microbial growth can arise during storage. Industrial products are frequently supplied in concentrated form and are normally diluted with water by the user. Microbial growth can lead to deterioration of the diluted product, costly interference with mechanical operations and expose the workers to possible skin irritation problems.

Aqueous personal care products, particularly emulsions and solutions having a pH of between about 5 and about 9, can support the growth of some undesirable microorganisms when sufficient water is present, unless an effective preservative is included Even anhydrous personal care products, such as eye shadows, lipsticks and pancake makeups which are repeatedly used, can be subjected to microbial contamination, especially when the product is moistened during use or adsorbs moisture on the exposed surface.

Cosmetic products, in particular, can be subject to microbial contamination during manufacture, packaging, storage, as well as during use. Consequently, there is a growing need for antimicrobial preservative systems having a broad spectrum of antimicrobial activity for use in almost all cosmetics. Desirably, the antimicrobial preservative system should be non-irritating to the skin and effective against those microorganisms of greatest concern over the range of pH values encountered in cosmetic products. Ideally, the antimicrobial preservative system should be cost effective and in a form that can be easily stored, shipped and incorporated into the product during its manufacture.

A number of antimicrobial preservatives suitable for cosmetics are well known from the cosmetic art and literature. A collection of articles discussing the categories of antimicrobial preservatives frequently used in cosmetics, and describing the properties and efficacy of commercially available preservatives can be found in the Preservatives Documentary/Encyclopedia issue of *Cosmet. & Toilet.*, 102, No. 12 (1987), the pertinent disclosures of which are incorporated herein by reference. For convenience, common category names will be used herein where applicable.

In particular, formaldehyde is known to have effective broad spectrum fungicidal and bactericidal activity. However, for cosmetic acceptability, antimicrobial preservation with formaldehyde is preferably provided by binding formaldehyde to a heterocyclic organic compound to be released slowly over time. These type of antimicrobial preservatives are commonly categorized as formaldehyde donors. A particularly effective formaldehyde donor commonly employed in cosmetics is a condensation product of formaldehyde and a hydantoin, namely, a 5,5-dimethylhydantoin-formaldehyde adduct having methylol functional groups bound to one or both of the nitrogen atoms of the hydantoin ring.

In commercial practice, 1,3-dimethylol-5,5dimethylhydantoin, is a popular broad-spectrum antimicrobial agent widely used in numerous cosmetics. This formaldehyde donor is designated the name of "DMDM Hydantoin" in the *CTFA Cosmetic Ingredient Dictionary*, Third Edition, (hereafter CTFA Dictionary) published in 1982 by The Cosmetic, Toiletry and Fragrance Association, Inc. (Washington, D.C.). For convenience, the CTFA name will be used.

Antimicrobial preservatives in liquid form are particularly desirable for convenient handling during manufacturing processes Until now, however, liquid DMDM Hydantoin was prepared commercially only as an aqueous solution resulting from the reaction of formaldehyde solution, such as formalin, with 5,5-dimethylhydantoin (DMH). Commercially, formalin is supplied as an aqueous solution of 37 percent by weight of formaldehyde usually with up to about 15 percent methanol added to prevent polymerization of the formaldehyde. A description of one commercial procedure can be found in U.S. Pat. No. 3,987,184 the pertinent disclosures of which are incorporated herein by reference.

Liquid aqueous DMDM Hydantoin, though useful, suffers from the following drawbacks. In commerce, solutions containing about 55 weight percent DMDM Hydantoin generally are not cold stable. The term "cold-stable" as used herein denotes a composition that does not tend to crystallize on standing, storage, or during shipping at a temperature of below about $-10$ degrees C. (below about 14 degrees F.). Moreover, the presence of water in the DMDM Hydantoin solution limits its utility to water-containing media.

There is a need and desire, therefore, for a cold-stable, water-free liquid antimicrobial preservative system comprising a formaldehyde donor, and DMDM Hydantoin in particular. One method aspect of this invention provides such a liquid antimicrobial preservative system prepared in a substantially anhydrous state which can be subsequently incorporated in a medium containing sufficient water to support microbial growth and effectively inhibit or retard such microbial growth.

From experience, the ideal preservation of aqueous personal care products requires a mixture of antimicrobial preservative compounds to effectively achieve broad spectrum activity against microbial growth. Each preservative compound, however, must be separately dissolved in the product during manufacture which adds to the cost and handling steps involved.

For example, other preservatives which are also widely used in commercial cosmetic practice are phenyl esters of parahydroxybenzoic acid and alkyl esters of parahydroxybenzoic acid containing 1 to about 10 carbon atoms in the alkyl group. These compounds are generally called "paraben esters" or "parabens". The term "paraben preservative" as used herein means that at least one paraben ester compound is present. Paraben preservatives have marked bacteriostatic activity against gram positive bacteria and a marked fungistatic activity, but efficacy against pseudomonads is poor. Typically, one or more of the paraben preservatives are also commonly included in products containing formaldehyde-donor preservatives to enhance broad spectrum antimicrobial efficacy.

The parabens, however, are generally supplied as solids which, though water-soluble, require heating to increase their solubility in water. There is a need and desire, therefore, for an antimicrobial preservative system including a formaldehyde donor and at least one paraben preservative, preferably in a clear liquid form, to eliminate the problems associated with dissolving solid preservatives during manufacturing. Another method aspect of this invention provides such a preservative system in substantially anhydrous liquid form.

SUMMARY OF THE INVENTION

This invention provides a method of preparing an antimicrobial preservative system containing a hydantoin-derived formaldehyde donor in substantially anhydrous liquid form. The formaldehyde donor is a condensation product of formaldehyde and a 5,5-disubstituted hydantoin compound having methylol functional groups attached to one or both of the nitrogen atoms of the hydantoin ring. Each substituent group on the C-5 position of the hydantoin compound independently can be a phenyl group or a lower alkyl group containing 1 to about 6 carbon atoms. Both substituent groups can be identical or different. Preferably each substituent group is a methyl group.

Briefly described, the method disclosed involves reacting formaldehyde with a 5,5-disubstituted hydantoin in a medium comprising a substantially anhydrous, yet water-miscible, solvent and an alkalizing agent at a temperature of above about 50 degrees C. (above about 122 degrees F.). The formaldehyde used in carrying out the reaction is in the form of substantially anhydrous paraformaldehyde. The amount of alkalizing agent included is sufficient to maintain a measurable diluted pH of above about 6 when one part by weight of the reaction mixture is diluted with about 9 to about 19 parts by weight water.

The reaction vessel is sealed to prevent the loss of volatile components until the reaction is completed. The reaction is judged completed when the reaction mixture contains less than about 2 percent by weight free formaldehyde. The cooled reaction provides an antimicrobial preservative system preferably having a measurable diluted pH of between about 6 and about 9.

The solvent can comprise a polyhydroxy alcohol containing from about 3 to about 6 carbon atoms, or an alkylene carbonate containing about 2 to about 3 carbon atoms, used alone or in combination.

In a particularly preferred method embodiment, a liquid antimicrobial preservative system comprising 1,3-dimethylol-5,5-dimethylhydantoin (DMDM Hydantoin) is prepared from a composition comprising paraformaldehyde, 5,5-dimethylhydantoin, substantially anhydrous propylene glycol and sodium hydroxide as an alkalizing agent. The amount of paraformaldehyde employed, calculated as formaldehyde, is at a ratio of about 2 moles formaldehyde per mole 5,5-dimethylhydantoin. The composition is preferably heated from about 60 degrees C. to about 105 degrees C. (from about 140 degrees F. to about 221 degrees F.). Sufficient alkalizing agent is included to preferably provide a measurable diluted pH of between about 6.5 and about 8.5 in the DMDM Hydantoin antimicrobial preservative system.

In another preferred embodiment, a liquid, substantially anhydrous antimicrobial preservative system comprising DMDM Hydantoin further including at least one paraben preservative therein can be prepared by practicing the principles of the method disclosed.

One advantage of the method disclosed is that it provides a substantially clear, liquid antimicrobial preservative system comprising a water-free and methanol-free formaldehyde donor. Moreover, this liquid system can be readily included in a non-aqueous medium because it is in substantially anhydrous form, and can be readily dissolved in an aqueous medium. A particular advantage is that a commercially desirable cold-stable antimicrobial preservative system containing DMDM Hydantoin, alone or in combination with a paraben preservative, can be prepared by the method disclosed and stored or shipped at winter-cold temperatures below about $-10$ degrees C. without crystallizing or precipitating.

A further benefit is that paraben preservative and DMDM Hydantoin can be provided in a single liquid preservative system thereby eliminating at least one manufacturing step and simplifying handling.

Still further advantages and benefits will be apparent to those skilled in the art from the description, examples and claims which follow.

DETAILED DESCRIPTION OF THE INVENTION

Antimicrobial preservative systems comprising a 5,5-disubstituted hydantoin having a methylol functional group attached to one or both of the nitrogen atoms of the hydantoin ring can be prepared in substantially anhydrous liquid form by the method of this invention. The substituent groups on the C-5 position of the hydantoin independently can be a lower alkyl group or a phenyl group. Preferably, each substituent group is a lower alkyl group, and each substituent group can be identical or different.

The term "lower alkyl" as used herein means that the alkyl group can contain 1 to about 6 carbon atoms. The term "substantially anhydrous" will be used interchangeably with the term "anhydrous" to denote that less than about 2 weight percent, more preferably less than about 1.5 weight percent of water is present in the liquid preservative system prepared by the method disclosed. With respect to paraformaldehyde, the term "substantially anhydrous" denotes paraformaldehyde which is at an active concentration of at above about 90 weight percent, preferably at about 95 weight percent or more.

Exemplary 5,5-disubstituted hydantoins include 5,5-dimethylhydantoin (DMH), 5-methyl-5-ethylhydantoin, 5,5diethylhydantoin, 5,5-diphenylhydantoin, 5-methyl-5phenylhydantoin, 5,5-pentamethylenehydantoin and the like known in the art as possessing broad spectrum bactericidal or fungicidal activity DMH is particularly preferred.

The present method will be generally illustrated by describing the preparation of 1,3-dimethylol-5,5-dimethylhydantoin (DMDM Hydantoin) at a concentration of from about 40 to about 75 weight percent in liquid form. This form is of most interest commercially and is not intended to limit the antimicrobial preservative system of this invention. It should be understood that the concentration of active antimicrobial preservative in a liquid system of this invention can be increased or decreased as desired by adjusting the amounts of reactants accordingly.

In the method disclosed, the mole amount of paraformaldehyde employed is calculated as moles of formaldehyde. Depending on the methylolation and amount of free formaldehyde desired, about 1 to about 3 moles formaldehyde per mole DMH can be reacted. It is recognized that higher or lower mole ratios of formaldehyde to DMH can be selected, if desired, without departing from the principles of this invention. The main criteria is that the liquid system obtained containing the condensation product of formaldehyde and DMH have antimicrobial activity when an antimicrobially effective amount is subsequently included in a medium containing sufficient water to support microbial growth.

The term "antimicrobially effective amount" as used herein denotes an amount capable of inhibiting or retarding microbial growth of those microorganisms of greatest concern in consumer products by preservative efficacy tests commonly used in the cosmetic and pharmaceutical arts.

Paraformaldehyde is a particularly preferred source of formaldehyde, because it is readily available commercially at concentrations of about 95 weight percent active in a non-dusting, prill form which is easy to handle. It is recognized that anhydrous formaldehyde gas can be used but this form of formaldehyde is less desirable and more difficult to handle safely during manufacturing.

For preparing a liquid preservative system containing about 55 to about 60 weight percent DMDM Hydantoin, sufficient paraformaldehyde is used to provide about 2 moles of formaldehyde per mole of DMH. The paraformaldehyde and DMH are dissolved in a substantially anhydrous medium. The medium comprises a substantially anhydrous solvent which is water-miscible and preferably non-toxic to humans and sufficient alkalizing agent to conduct the reaction at a measurable diluted pH of above about 6, preferably between about 6.25 and about 10, more preferably between about 6.5 and about 9, most preferably between about 7 and about 8. The term "measurable diluted pH" refers to the pH of the reaction mixture measured after diluting one part by weight of the liquid reaction mixture with about 9 to about 19 parts by weight of deionized water.

Useful substantially anhydrous solvents which are water-miscible include polyhydroxy alcohols containing about 3 to about 6 carbon atoms and alkylene carbonates containing about 2 to about 3 carbon atoms in the alkylene radical. These solvents can be used alone or in combination. Polyhydroxy alcohols are particularly preferred for personal care products for use on skin or hair.

Water-miscible polyhydroxy alcohols which are suitable for practicing the method include those commonly used in consumer products, such as propylene glycol, glycerine, butylene glycol and hexylene glycol, used alone or in combination. Propylene glycol is particularly preferred. Exemplary water-miscible alkylene carbonates useful for practicing the disclosed method include ethylene carbonate and propylene carbonate, alone or in combination.

One preferred method embodiment for preparing the DMDM Hydantoin comprises the following steps. A substantially anhydrous composition is prepared by dissolving the calculated amounts of paraformaldehyde and DMH in a medium comprised of substantially anhydrous propylene glycol and alkalizing agent with stirring in a reactor outfitted for heating and cooling and for sealing against loss of volatile components.

The composition is heated above about 50 degrees C. (above about 122 degrees F.), preferably from about 60 degrees C. to about 110 degrees C. (from about 140 degrees F. to about 230 degrees F.), more preferably from about 70 degrees C. to about 105 degrees C. (from about 158 degrees F. and about 221 degrees F.) to provide a substantially clear, heated reaction mixture. It is recognized that higher temperatures can be used but are not desirable, because they increase the formation of antimicrobially ineffective resinous formaldehyde-hydantoin adducts and present manufacturing difficulties. The reactor is sealed, and the temperature and measurable diluted pH of the clear reaction mixture are maintained until the reaction is complete. The reaction can be completed in a period of from about 1/2 hour to about 12 hours; the reaction generally proceeding more rapidly at increased temperatures. Preferably the reaction is completed within a practical period of between about 1 and about 5 hours.

The measurable diluted pH of the reaction mixture can be maintained by sampling a portion of the heated reaction mixture after a clear reaction mixture has formed as described earlier. If the measurable diluted pH is too acidic, a sufficient amount of alkalizing agent is added. Conversely, if the measurable pH is too alkaline, a sufficient amount of an acidifying agent can be added.

The term "alkalizing agent" refers to any commercially practical alkaline base which does not interfere with the preparation of an antimicrobially active preservative system and which, if present in an amount in excess of that needed for pH adjustment, is preferably soluble in the solvent medium and is substantially nontoxic to humans. For example, the alkalizing agent can be an alkali metal hydroxide, such as sodium hydroxide or potassium hydroxide; an alkali metal salt, such as sodium carbonate or sodium methylate; an alkaline earth hydroxide, such as calcium hydroxide or magnesium hydroxide, or an organic base, such as a water-soluble alkylamine or an alkanolamine having 1 to about 4 carbon atoms in the alkyl or alkanol radical commonly used in cosmetics, such as dimethylamine, diethylamine, monoethanolamine, diethanolamine, triethanolamine, monoisopropanolamine, diisopropanolamine, triisopropanolamine and the like. Sodium hydroxide is particularly preferred and is added as a concentrated, caustic solution of about 50 weight percent. Thus, less than about 1 weight percent caustic solution is generally needed.

Likewise, the term "acidifying agent" refers to any commercially practical acid that does not interfere with the preparation of an antimicrobially active preservative system and, which if present in an amount in excess of that needed for pH adjustment, is preferably soluble in the solvent medium and is substantially nontoxic to humans. For example, acids commonly used in cosmetics include organic water-soluble polyhydroxy acids, such as lactic acid, citric acid, and tartaric acid; and inorganic acids, such hydrochloric acid, phosphoric acid and sulfuric acid. The reaction is considered to be complete when the amount of free formaldehyde is below about 2 weight percent, preferably below about 1.5 weight percent.

Completion is determined by periodically sampling the reaction mixture and analyzing for the amount of free formaldehyde. Free formaldehyde can be determined by analytical methods well known in the art, such as by hydroxylamine hydrochloride titration method. The terms "free formaldehyde," as used herein, refer to the excess (unbound) formaldehyde present from the hydrolysis of paraformaldehyde. The terms "total formaldehyde," as used herein, refers to the sum of the free formaldehyde and the available formaldehyde from the hydrolysis of the methylol functional groups.

After the reaction is completed, the reaction mixture is cooled to about 25 degrees C. (about 77 degrees F.), collected, and filtered, if desired, to provide an antimicrobial preservative system. The antimicrobial preservative system obtained by the method disclosed is a substantially clear liquid that is relatively free of formaldehyde odor and is substantially anhydrous. Preferably, a 55 weight percent DMDM Hydantoin preservative system obtained by the foregoing method has a free formaldehyde content of below about 2 weight percent, a total formaldehyde content of above about 17 weight percent, a water content of below about 2 weight percent, and a cloud point preferably below about −20 degrees C. (below about −4 degrees F.), more preferably below about −50 degrees C. (below about −58 degrees F.). Preferably the measurable diluted pH of the DMDM Hydantoin preservative system is between about 6.5 and about 8.5, more preferably between about 7 and about 8, when one part by weight is diluted with about 9 to about 19 parts by weight of deionized water.

It is well recognized in the art that the actual effective antimicrobial amount of the DMDM Hydantoin preservative system required in a product will depend on a number of factors, among which the presence of water is a major factor, contributing to the support of microbial growth. However, the amount of preservative needed is readily determinable by persons skilled in the formulation and preparation of consumer products.

In another embodiment, an antimicrobial preservative system obtained by the method disclosed can provide a combination of a formaldehyde donor preservative and a paraben preservative in a single antimicrobial preservative system. Useful paraben preservatives include, without limitation, phenyl esters of parahydroxybenzoic acid, alkyl esters of parahydroxybenzoic acid containing 1 to about 10 carbon atoms in the alkyl group, and derivatives thereof used alone or combination. Exemplary paraben preservatives include methyl paraben, ethyl paraben, propyl paraben, isopropylparaben, butylparaben, isobutylparaben, isodecylparaben, phenoxyethylparaben, benzyl paraben, and the like.

For this purpose, at least one paraben preservative is preferably included in the substantially anhydrous antimicrobial preservative system comprising the formaldehyde donor obtained by the method disclosed. The amount of paraben to be included is limited only by the solubility of the paraben compound in the medium. This advantageously provides paraben preservative and DMDM Hydantoin in combination, each at a relatively high concentration, in a single liquid antimicrobial preservative system.

For example, methyl paraben can be included in amounts of from about 10 to about 20 weight percent in an antimicrobial preservative system of this invention comprising about 55 to about 70 weight percent DMDM Hydantoin prepared with a medium comprising propylene glycol by dissolving the methyl paraben in the liquid DMDM Hydantoin prepared by the disclosed method, preferably warming to about 50 degrees C. (about 122 degrees F.) to hasten solubilization.

Alternatively, the desired paraben preservative can be dissolved in a portion of the solvent previously withheld from the medium and then blended with the DMDM Hydantoin prepared by the disclosed method. Preferably, the desired paraben preservative is included during the preparation of the DMDM Hydantoin after the DMDM Hydantoin reaction is complete by dissolving the paraben compound in the reaction mixture while cooling the reaction mixture when the temperature thereof is favorable for such solubilization.

It was found that an antimicrobial preservative system comprising about 55 to about 65 weight percent active DMDM Hydantoin prepared by the method disclosed was coldstable. It was surprisingly found that no crystallization occurred at temperatures below about −50 degrees C. (below about −58 degrees F.), even when combined with about 15 to about 20 weight percent methyl paraben preservative.

The formation of DMDM Hydantoin can be confirmed by various analytical techniques well known in the art, such as gas chromatography, infrared spectroscopy, ultraviolet spectroscopy, nuclear magnetic spectroscopy and differentiated scanning calorimetry. Infrared spectroscopy is preferred.

DMDM Hydantoin is a known cosmetic preservative generally described as being a broad-spectrum antimicrobial agent, effective in inhibiting or retarding the growth of yeast, gram-positive bacteria and gram-negative bacteria in water-containing medium. DMDM Hydantoin is present in hundreds of product formulations, particularly personal care products, typically in an antimicrobially sufficient quantity of from about 0.01 to about 1 weight percent. The preservative efficacy of DMDM Hydantoin prepared by the present method was judged substantially equivalent to or greater than that of corresponding DMDM Hydantoin prepared by conventional aqueous method with formalin. This was based on comparative preservative effectiveness assay tests of the inhibition of the growth of a mold, Aspergillus niger, and a yeast, Candida albicans in a relatively "mild" shampoo model. The tests were conducted for a period of about 1 week employing active concentrations of DMDM Hydantoin of from about 0.02 to about 0.1 weight percent.

The following Examples illustrate a liquid antimicrobial preservative system of this invention with generally preferred ingredients and methods of preparation, but are not intended to be limited thereby.

EXAMPLE 1

This example illustrates one method embodiment of preparing a substantially anhydrous liquid antimicrobial preservative system comprising about 55 weight percent 1,3-dimethylol-5,5-dimethylhydantoin (DMDM Hydantoin). The following composition was prepared.

| Component | Weight Percent (as supplied) |
| --- | --- |
| 1. Propylene glycol | 44.8 |
| 2. Paraformaldehyde Prills (95%) | 18.2 |
| 3. 5,5-Dimethylhydantoin | 36.5 |
| 4. Sodium hydroxide (50% in water) | 0.5 |

Ingredient No. 1 was charged into a sealable reaction vessel outfitted with a jacket for heating or cooling, a mixing agitator and a sampling port. Ingredients No. 2 and 3 were added and dissolved with mixing agitation followed by admixing in ingredient No. 4. The measurable diluted pH of the composition was between about 8.0 and about 8.5. Then, while continuing the mixing agitation, the composition was heated to about 100 degrees C. (about 212 degrees F.) at which temperature the reactor was sealed to prevent loss of volatile components, and formaldehyde in particular, from the heated reaction mixture.

The heated reaction mixture was maintained at the foregoing temperature for about thirty minutes or until the appearance of the mixture was substantially visually clear. A portion of the heated clear mixture was sampled, and 10 grams of sample were diluted with 90 grams of deionized water for determining the measurable diluted pH. The measurable diluted pH was maintained at between about pH 6.5 and about 7.5.

The temperature of the heated, clear reaction mixture was maintained at about 100 degrees C. (about 212 degrees F.) under mixing agitation for about 5 hours or until formation of the DMDM Hydantoin was substantially completed. The amount of free formaldehyde was periodically determined at about hourly intervals and the reaction was judged completed when the amount of free formaldehyde was below about 2 weight percent. The reaction mixture was then cooled to about 25 degrees C. (about 77 degrees F.), assayed and collected.

The amount of free formaldehyde present in the liquid DMDM Hydantoin preservative system obtained was about 1.7 weight percent, the total formaldehyde was about 17.3 weight percent. Total water content was less than about 1.2 weight percent, determined by Karl Fischer method.

The substantially anhydrous 55 weight percent DMDM Hydantoin preservative system obtained by this method was a substantially water-white visually clear liquid having a cloud point of below about −50 degrees C. (below about −58 degrees F.). The liquid preservative system dissolved easily in water and, when 1 part by weight was diluted with 9 parts by weight of deionized water, had a pH of about 7.5. The product was substantially free of formaldehyde odor. The liquid preservative system remained physically clear on standing at ambient room temperature for about 4 ½ months and in the cold, at a temperature of below about −10 degrees C. (below about 14 degrees F.) for about 4 weeks.

EXAMPLE 2

This example illustrates the preparation of another substantially anhydrous liquid antimicrobial preservative system comprising about 65 weight percent DMDM Hydantoin by a method of this invention. The following composition was prepared as described below.

| Component | Weight Percent (as supplied) |
| --- | --- |
| 1. Propylene glycol | 35.1 |
| 2. Paraformaldehyde Prills (95%) | 21.4 |
| 3. 5,5-Dimethylhydantoin | 42.9 |
| 4. Sodium hydroxide (50% in water) | 0.6 |

The procedure of Example 1 was followed except that the composition was heated to about 105 degrees C. (about 221 degrees F.). A substantially clear, substantially anhydrous liquid 65 weight percent DMDM Hydantoin preservative system was obtained.

EXAMPLE 3

This example illustrates another method embodiment of preparing a substantially anhydrous liquid antimicrobial preservative system comprising about 55 weight percent DMDM Hydantoin. The following composition was prepared as described below.

| Component | Weight Percent (as supplied) |
| --- | --- |
| 1. Propylene glycol | 44.7 |
| 2. Sodium Hydroxide (50% in water) | 0.6 |
| 3. Paraformaldehyde Prills (95%) | 18.2 |
| 4. 5,5-dimethylhydantoin | 36.5 |

Ingredient No. 1 was charged into a sealable reaction vessel outfitted as described in Example 1 and made alkaline by admixing therein ingredient No. 2. Ingredient Nos. 3 and 4 were then slowly admixed into the alkaline medium. Mixing agitation was continuously maintained and the contents of the reactor were heated to about 50 degrees C. (about 122 degrees F.) at which temperature, the reactor was sealed to prevent evaporation of the volatile components, particularly formaldehyde.

The warmed reaction mixture was further heated to about 90 degrees C. (about 194 degrees F.) and maintained at that temperature for about 12 hours until the reaction was complete. Thereafter, the reaction mixture was cooled to about 25 degrees C. (about 77 degrees F.), assayed, filtered and collected.

A substantially anhydrous water-white clear liquid was obtained having a cloud point of below about −5 degrees C. (below about 23 degrees F.), and a measurable diluted pH of between about 7 and about 8 when 5 grams of liquid sample were diluted with 95 grams of deionized water. The amount of free formaldehyde was about 1.7 weight percent and total formaldehyde was about 17.3 weight percent.

EXAMPLE 4

This example illustrates the preparation of four anhydrous preservative systems (A-D) comprising a combination of DMDM Hydantoin and methyl paraben preservative.

| Component | Percent By Weight | | | |
| --- | --- | --- | --- | --- |
| | A | B | C | D |
| DMDM Hydantoin of Example 1 | 85 | 86.6 | 90 | — |
| DMDM Hydantoin of Example 2 | — | — | — | 85 |
| Methyl Paraben | 15 | 13.4 | 10 | 15 |

The methyl paraben was admixed directly into the DMDM Hydantoin preservative system by adding the methyl paraben directly with stirring and warming to about 50 degrees C. (about 122 degrees F.) to hasten solubilization. All combinations produced substantially clear liquid systems. Preservative system (A) also was stored at a temperature of below about −50 C. (below about −58 F.) overnight and was judged cold-stable.

The present invention has been described generally and with respect to preferred embodiments. It will be understood that modifications and variation of tho disclosed method and compositions may be made without departing from the spirit and scope of the novel concept of the present invention.

What is claimed is:

1. A cold stable antimicrobial preservative system in substantially anhydrous liquid form which is dissolvable in an antimicrobially effective amount in a medium capable of supporting microbial growth comprising:
   (a) as an active preservative, a condensation product of formaldehyde and a 5,5-disubstituted hydantoin wherein each such substituent group on the hydantoin ring is independently selected from the group consisting of phenyl and lower alkyl containing 1 to about 6 carbon atoms, said condensation product having a methylol functional group attached to one or both nitrogen atoms on the hydantoin ring;
   (b) a substantially anhydrous, water-miscible solvent selected from the group consisting of polyhydroxy alcohols having about 3 to about 6 carbon atoms per molecule, alkylene carbonates having about 2 to about 3 carbon atoms in the alkylene radical thereof per molecule, and mixtures thereof; and
   (c) sufficient alkalizing agent to provide a pH between about 6 and about 9 when one part by weight of said liquid preservative system is diluted with about 9 to about 19 parts by weight of deionized water.

2. The antimicrobial preservative system of claim 1 further containing at least one paraben preservative.

3. The antimicrobial preservative system of claim 1 having a free formaldehyde content below about 2 weight percent.

4. The antimicrobial preservative system of claim 1 wherein said solvent is a polyhydroxy alcohol selected from the group consisting of propylene glycol, glycerine, butylene glycol, hexylene glycol and mixtures thereof.

5. The antimicrobial preservative system of claim 1 wherein said solvent is an alkylene carbonate selected from the group consisting of ethylene carbonate, propylene carbonate and mixtures thereof.

6. The antimicrobial preservative system of claim 1 where each said substituent group is an alkyl group and both said alkyl groups are identical.

7. The antimicrobial preservative system of claim 1 wherein said condensation produce comprises 1,3-dimethylol-5,5-dimethylhydantoin.

8. The antimicrobial preservative system of claim 1 wherein said solvent is propylene glycol and said alkalizing agent is an alkali metal hydroxide.

9. The antimicrobial preservative system of claim 8 wherein said condensation product is 1,3-dimethylol-5,5-dimethylhydantoin present at a concentration of about 40 to about 75 weight percent on a total system weight basis and said system has a diluted pH of about 6.5 to about 8.5.

10. The antimicrobial preservative system of claim 8 further containing dissolved therein at least one paraben preservative selected from the group consisting of phenyl esters of parahydroxybenzoic acid, alkyl esters of parahydroxybenzoic acid containing 1 to about 10 carbon atoms in the alkyl group, and derivatives and mixtures thereof.

11. The antimicrobial preservative system of claim 10 wherein said paraben preservative is methylparaben.

12. A preservative system of claim 7 that is incorporated in an amount in the range of about 0.01 weight percent to about 1 weight percent into a personal care product.

13. A preservative system of claim 7 that is incorporated in an amount in the range of about 0.01 weight percent to about 1 weight percent into a household product.

14. A preservative system of claim 7 that is incorporated in an amount in the range of about 0.01 weight percent to about 1 weight percent into an industrial product.

15. An aqueous medium capable of supporting microbial growth containing the preservative system of claim 1 in an effective antimicrobial amount.

16. An aqueous medium capable of supporting microbial growth containing the preservative system of claim 2 in an effective antimicrobial amount.

17. A method for preparing a substantially anhydrous liquid antimicrobial preservative composition comprising the steps of sequentially:

(a) dissolving each of paraformaldehyde and a 5,5-disubstituted hydantoin wherein each such substituent is independently selected from the group consisting of phenyl and lower alkyl containing less than 7 carbon atoms in a substantially anhydrous, water-miscible solvent selected from the group consisting of polyhydroxy alcohols each having about 3 to about 6 carbon atoms per molecule, alkylene carbonates each having about 2 to about 6 carbon atoms per molecule, and mixtures thereof, together with sufficient alkalizing agent to provide a substantially anhydrous liquid composition having a pH above about 6 when diluted with about 9 to about 19 parts by weight of deionized water;

(b) heating said liquid composition to a temperature above about 50 degrees C. to provide a heated liquid reaction mixture which is substantially visually clear;

(c) maintaining said liquid reaction mixture at said temperature and said diluted pH until reaction between said paraformaldehyde and said hydantoin is substantially complete based on a determination of the amount of free formaldehyde present in said reaction mixture, said reaction being substantially complete when the amount of said free formaldehyde is below about 2 weight percent based on total weight of said reaction mixture; and (d) cooling and optionally filtering the so-cooled said resulting reaction mixture to provide such a substantially anhydrous liquid antimicrobial preservative composition, said preservative composition being characterized by:

(1) containing a condensation product of said paraformaldehyde and said hydantoin wherein methylol functional groups are attached to at least one of the two nitrogen atoms of the ring of said hydantoin, and (2) having a capacity to inhibit and/or retard the growth of undesirable microorganisms when an antimicrobially effective amount thereof is subsequently included in a medium capable of supporting microbial growth.

18. The antimicrobial preservative system obtained from the method of claim 17.

19. The method of claim 17 further including the step of including at least one paraben preservative in the substantially anhydrous liquid antimicrobial preservative system after step (c) at a temperature favoring dissolution of the paraben preservative either while the reaction mixture is cooling in step (d) or in an added step (e).

20. The antimicrobial preservative system obtained from the method of claim 19.

21. The antimicrobial preservative system of claim 20 wherein the included paraben ester is selected from the group consisting of phenyl esters of parahydroxybenzoic acid, alkyl esters of parahydroxybenzoic acid having 1 to about 10 carbon atoms in the alkyl group, and derivatives thereof, used alone or in combination.

22. The antimicrobial preservative system obtained from the method of claim 17 wherein the condensation product comprises 1,3-dimethylol-5,5-dimethyl hydantoin, the solvent is a polyhydroxy alcohol selected from the group consisting of propylene glycol, glycerine, butylene glycol, and hexylene glycol, used alone or in combination and the alkalizing agent is an alkali metal hydroxide.

23. A substantially anhydrous liquid antimicrobial preservative system of claim 1 wherein said preservative comprises 1,3-dimethylol-5,5-dimethyl-hydantoin obtained by the reaction of 5,5-dimethylhydantoin with about 1 to about 3 moles of paraformaldehyde calculated as formaldehyde per mole of said 5,5-dimethylhydantoin in a substantially anhydrous medium comprising propylene glycol and sodium hydroxide.

24. A method of inhibiting or retarding microbial growth in a consumer product requiring preservation against microbial growth, the method comprising incorporating into the product an effective microbial inhibiting amount of the substantially anhydrous antimicrobial preservative system of claim 1.

25. The method of claim 24 wherein the antimicrobial preservative system comprises 1,3-dimethylol-5,5-dimethylhydantoin.

26. The method of claim 25 wherein the antimicrobial preservative system further includes at least one paraben preservative.

27. The method of claim 34 wherein said liquid composition contains 5,5-dimethylhydantoin as said hydantoin and about 1 to about 3 moles of said paraformaldehyde, calculated as formaldehyde, per mole of said 5,5-dimethylhydantoin, said solvent comprises a substantially anhydrous polyhydroxy alcohol having about 3 to about 6 carbon atoms per molecule, said temperature is in the range of about 50 degrees C. to about 110 degrees C. and said method is carried out in a sealed reaction vessel.

28. The method of claim 27, wherein said condensation product is 1,3-dimethylol-5,5-dimethylhydantoin.

29. The method of claim 28, wherein said 1,3-dimethylol-5,5-dimethylhydantoin is present at about 40 to about 75 weight percent, the polyhydroxy alcohol is propylene glycol and the alkalizing agent is sodium hydroxide.

30. An antimicrobial preservative system produced by the process of claim 34 wherein said 5,5-disubstituted hydantoin is 5,5-dimethylhydantoin, and said preservative system contains 1,3-dimethylol-5,5-dimethylhydantoin.

31. The system of claim 30 which contains about 55 to about 75 weight percent of said 1,3-dimethylol-5,5-dimethylhydantoin and has a free formaldehyde content of less than about 2 weight percent on a total system weight basis.

32. The system of claim 31 wherein said liquid composition is heated at a temperature in the range of about 60 degrees C. to about 110 degrees C.

33. The system of claim 30 further containing at least one paraben preservative.

* * * * *

UNITED STATES PATENT AND TRADEMARK OFFICE
CERTIFICATE OF CORRECTION

PATENT NO. : 5,037,843

DATED : August 6, 1991

INVENTOR(S) : Thomas G. Schoenberg

It is certified that error appears in the above-identified patent and that said Letters Patent is hereby corrected as shown below:

Col. 14, line 29, claim 27, after "claim"
   change "34" to --17--.

Col. 14, line 47, claim 30, after "claim"
   change "34" to --17--.

Signed and Sealed this

Ninth Day of March, 1993

Attest:

STEPHEN G. KUNIN

Attesting Officer     Acting Commissioner of Patents and Trademarks